US012521125B2

(12) United States Patent
Ruisz et al.

(10) Patent No.: US 12,521,125 B2
(45) Date of Patent: Jan. 13, 2026

(54) HAND-HELD SHAFT-TYPE SURGICAL INSTRUMENT

(71) Applicant: Aesculap AG, Tuttlingen (DE)

(72) Inventors: Martin Ruisz, Tuttlingen (DE); Bernhard Kupferschmid, Emmingen-Liptingen (DE)

(73) Assignee: Aesculap AG, Tuttlingen (DE)

( * ) Notice: Subject to any disclaimer, the term of this patent is extended or adjusted under 35 U.S.C. 154(b) by 313 days.

(21) Appl. No.: 18/030,169

(22) PCT Filed: Sep. 29, 2021

(86) PCT No.: PCT/EP2021/076759
§ 371 (c)(1),
(2) Date: Apr. 4, 2023

(87) PCT Pub. No.: WO2022/073817
PCT Pub. Date: Apr. 14, 2022

(65) Prior Publication Data

US 2024/0023974 A1 Jan. 25, 2024

(30) Foreign Application Priority Data

Oct. 5, 2020 (DE) ..................... 10 2020 126 015.6

(51) Int. Cl.
*A61B 17/16* (2006.01)

(52) U.S. Cl.
CPC ................................ *A61B 17/1611* (2013.01)

(58) Field of Classification Search
CPC ........................ A61B 17/1611; A61B 17/1608
See application file for complete search history.

(56) References Cited

U.S. PATENT DOCUMENTS 6,638,280 B2 * 10/2003 Agbodoe ........... A61B 17/1611
606/171
7,052,505 B2 5/2006 Widmann
9,168,046 B2 10/2015 Weisshaupt et al.
(Continued)

FOREIGN PATENT DOCUMENTS

DE 102009008691 A1 8/2010
DE 102012209247 A1 12/2013
(Continued)

OTHER PUBLICATIONS

Search Report received in German Application No. 10 2020 126 015.6 dated May 6, 2021, with translation, 9 pages.
(Continued)

*Primary Examiner* — Erin Mcgrath
(74) *Attorney, Agent, or Firm* — Christopher A. Rothe; CM Law

(57) ABSTRACT

A hand-held sliding shaft-type surgical instrument includes a shaft, in which a longitudinal groove is formed extending over the length of the shaft, and a slide, which is movably mounted in the longitudinal groove. Relative movement of the slide in the longitudinal groove is at least partly guided by at least one connecting piece that constricts the longitudinal groove in the width direction. The shaft has a cleaning recess in the region of the connecting piece in the longitudinal direction. The cleaning recess forms a radial through-opening that opens into the longitudinal groove from the groove base side.

14 Claims, 2 Drawing Sheets

(56) References Cited

U.S. PATENT DOCUMENTS

| | | | |
|---|---|---|---|
| 2007/0093843 | A1 | 4/2007 | Schneiter |
| 2013/0325015 | A1 | 12/2013 | Grasshoff |

FOREIGN PATENT DOCUMENTS

| | | | |
|---|---|---|---|
| EP | 1363542 | B1 | 10/2007 |
| EP | 2226021 | A2 | 9/2010 |
| JP | 2012516730 | A | 7/2012 |
| WO | 9505123 | A1 | 2/1995 |

OTHER PUBLICATIONS

Search Report received in International Application No. PCT/EP2021/076759 dated Dec. 13, 2021, with translation, 5 pages.
Written Opinion received in International Application No. PCT/EP2021/076759 dated Dec. 13, 2021, with translation, 9 pages.
Communication received in European Application No. 21 783 282.3-1122 dated Apr. 3, 2025, with translation, 8 pages.
Office Action received in Japanese Application No. 2023-520483 dated Mar. 5, 2025, with translation, 24 pages.

* cited by examiner

HAND-HELD SHAFT-TYPE SURGICAL INSTRUMENT

CROSS-REFERENCE TO RELATED APPLICATIONS

This application is the United States national phase entry of International Application No. PCT/EP2021/076759, filed Sep. 29, 2021, and claims priority to German Application No. 10 2020 126 015.6, filed Oct. 5, 2020. The contents of International Application No. PCT/EP2021/076759 and German Application No. 10 2020 126 015.6 are incorporated by reference herein in their entireties.

FIELD

The present disclosure relates to a medical, in particular hand-held surgical instrument with sliding shaft/sliding-shaft instrument for transmitting an actuating force or motion to an instrument effector.

The present disclosure relates to any type of surgical instrument having a sliding shaft.

BACKGROUND

Such a sliding-shaft instrument may be, for example, biopsy forceps, scissors, bone punches, or similar hand instruments. They are used, for example, for cutting, shearing or clamping procedures in the human or animal body. In this case, a slide is moved along a guide of a shaft via corresponding hand grips in order to actuate, in particular to open and close, a (jaw-like) effector at a distal end of the sliding shaft. Such sliding-shaft instruments are thus characterized by having an elongated shaft/a shaft extending in the longitudinal direction, on/in which a slide is slidably arranged in the longitudinal direction of the shaft. The slide and the shaft are typically slidingly connected to each other via a guide arranged or formed on/in the shaft and guiding a movement of the slide along the shaft, but preventing further relative movements of the slide relative to the shaft. Such a surgical sliding-shaft instrument is known, for example, from EP 1 363 542 B1.

In addition, DE 10 2009 008 691 A1 discloses a sliding-shaft instrument with a longitudinal groove in the shaft with a T-shaped cross section, in which a corresponding projection on the lower side of the slide engages in a form-fitting manner.

In order to be able to reuse sliding-shaft instruments, the sliding-shaft instrument has to be at least cleaned and/or often even sterilized. Due to the tight guiding of the slide on/in the shaft, however, it has so far not been possible, or at least only with difficulty, to reprocess the sliding shaft reproducibly without first disassembling the instrument into its individual parts. However, the disassembly of a sliding shaft, which usually has a narrow tolerance, means that the individual parts may be damaged during assembly, so that the sliding-shaft instrument can no longer meet the required tolerances, at least after a certain number of disassembly cycles. For this reason, sliding-shaft instruments or their sliding shafts are not normally disassembled for cleaning.

However, in order to create the necessary free spaces in the sliding shaft for cleaning/sterilization in the assembled state, a known sliding shaft has radial bores spaced along the entire length of the shaft, which connect a space in the shaft housing the slide with the surroundings for improved flushing of the slide with cleaning fluid or a sterilization medium, but which considerably reduce the stability of the shaft and are costly to manufacture due to the large number of burrs. It is also known that instead of having several radial bores, a longitudinal groove which houses the slide can be widened by lateral milling, resulting in longitudinally spaced, narrow abutment/contact/sliding points in/on the shaft, whereby the shaft can be cleaned in the longitudinal portions between the contact points with a brush down to the depth of the longitudinal groove ground, but this does not yet ensure sufficient, reproducible reprocessability of the sliding shaft.

SUMMARY

It is therefore the object of the invention to provide a sliding shaft for a surgical sliding-shaft instrument as well as a surgical sliding-shaft instrument which can be reprocessed in a reproducible manner without disassembling the sliding shaft in order to enable reuse, and at the same time fulfills the requirements with regard to functionality, ease of manufacture, high precision and stability of a sliding shaft or of a sliding-shaft instrument.

The core of the disclosure therefore consists in forming the axially spaced abutment/contact/sliding points known per se from the prior art between the groove side wall of the shaft and the slide in a substantially triangular shape with concave side edges when viewed in a longitudinal section of the shaft and additionally forming radial openings in the shaft from the groove ground side to the groove ground in the regions of the abutment/contact/sliding points formed in this way. This configuration allows each abutment/contact/sliding point to extend over a greater distance than in the prior art, preferably beyond the respective radial opening on both sides in the axial direction of the shaft, thereby keeping the shaft stiff despite the additional radial openings. Due to the concavity, the abutment/contact/sliding points taper very quickly in the axial direction, which improves flushing with cleaning fluid and/or sterilization medium and also enables penetration of the cleaning fluid and/or of sterilization medium into the gap between the groove ground and the slide via the radial openings.

However, the particularity of this embodiment also lies in its ease of manufacture. Accordingly, another core of the disclosure is to produce the axially spaced abutment/contact/sliding points by milling circular segment-shaped grooves in/out from below the groove ground to beyond the groove ground via a shaft/circle cutter, resulting in essentially rectangular openings at the groove ground and additionally concavely shaping one side edge of the triangular-shaped abutment/contact/sliding point. Preferably, the same cutter is used to mill into the shaft/shaft groove from above the groove ground in such a way that the two side edges of the abutment/contact/sliding points facing away from the groove ground are also given the aforementioned concave shape.

More precisely, the medical, in particular hand-held surgical instrument has a sliding shaft. The sliding shaft has an elongated shaft and a slide (longitudinally) displaceable thereon, i.e. arranged along the longitudinal direction of the shaft. The sliding shaft serves to couple an actuation of a tool head/tool portion/effector of the sliding-shaft instrument with an actuation of an instrument handle of the sliding-shaft instrument. In particular, the sliding shaft is connected or connectable to the tool head arranged at a distal end of the sliding shaft such that the tool head can be actuated, in particular opened and closed, by the relative displacement of the slide relative to the shaft. In addition, the sliding shaft is in particular connected or connectable to the instrument handle such that the slide can be longitudinally displaced relative to the shaft by the actuation of the instrument handle, such as by a pivoting of a first hand grip relative to a second hand grip. The slide is housed in a longitudinal groove of the shaft (longitudinally displaceable). The longitudinal groove is open towards a circumferential side of the shaft. The slide is preferably plate-shaped, for example as a sliding plate. The relative displacement of the slide relative to the shaft is guided by at least one crosspiece (abutment/contact/sliding point) of the shaft. The crosspiece narrows the longitudinal groove in the width direction in sections from both sides of the slide to guide the slide on both sides. In particular, the shaft may therefore have at least one pair of crosspieces arranged opposite each other in the width direction of the groove for guiding the slide. Preferably, the crosspieces (the pair of crosspieces) arranged in pairs are spaced apart from each other by a thickness of the slide in the width direction of the groove. In this way, the slide can slide on both its sides against one crosspiece of each pair of crosspieces. The slide is preferably arranged centrally in the width direction of the groove in the longitudinal groove.

According to the present disclosure, the shaft has a cleaning recess (recess milled in/out) in the longitudinal direction in the region of the crosspiece (or of the pair of crosspieces, respectively), wherein said cleaning recess forms a through hole (rectangular radial opening) opening into the longitudinal groove. In particular, the cleaning recess may be open to a circumferential side of the shaft (hereinafter referred to as the lower side) facing away from the radial groove opening. By forming a passage between the cleaning recess and the longitudinal groove, a flow of cleaning fluid, for example from top to bottom or from bottom to top, through the shaft and around the slide is made possible. The cleaning recess is arranged in the longitudinal direction in the region of the crosspiece, i.e. in the longitudinal direction at the height of the crosspiece. By arranging the additional cleaning recess in the region of the crosspiece, in which there is more shaft material than in the other regions of the longitudinal groove, the stability is only slightly reduced and a sufficiently high stability of the shaft is ensured. Preferably, the cleaning recess may be configured/milled as a milled recess. In this way, for example in contrast to bores, a flatter surface can be produced and, for example, the occurrence of burrs can be reduced. The cleaning recess is preferably arranged centrally in the shaft in the width direction. The cleaning recess is preferably elongated. This removes as little material as possible from the shaft in its more unstable width direction for the cleaning recess.

In other words, the shaft has a longitudinal groove in which the slide is longitudinally displaceable and which widens along the longitudinal direction in sections in the width direction (by a gap) or narrows/tapers in sections in the width direction (by the crosspiece). The gap is thus narrowed or interrupted in sections in the longitudinal direction by the crosspiece. This means that the longitudinal groove has a basic width corresponding to a distance between two crosspieces of a pair of crosspieces or a thickness of the slide, respectively. In addition, the longitudinal groove has a greater width than the basic width in sections along the longitudinal direction, i.e. the longitudinal groove widens in sections. In the widened sections of the longitudinal groove, the slide is not guided through the shaft. Thus, a gap is formed between the slide and the shaft in the widened sections. The gap can be regarded as part of the longitudinal groove.

In yet other words, the shaft has a longitudinal groove opening to an upper side of the shaft and a cleaning recess opening to the lower side of the shaft (as defined above). Thereby, the cleaning recess extends so far into the shaft, in particular into the longitudinal groove, that a flow from the upper side to the lower side (or from the lower side to the upper side, respectively) and thus improved cleanability is possible.

According to a preferred embodiment, the shaft may preferably have multiple crosspieces (or pairs of crosspieces, respectively) spaced apart in longitudinal direction depending on the length of the sliding shaft (and/or the thickness of the slide) along the longitudinal groove. Preferably, the multiple crosspieces (or pair of crosspieces) are spaced at equal intervals in the longitudinal direction. This prevents the slide from kinking. Preferably, the shaft has multiple cleaning recesses, in particular one cleaning recess per crosspiece (or pair of crosspieces).

According to a preferred embodiment, the sliding shaft may have a gap for cleaning formed in the width direction between the slide and the shaft, in particular by the longitudinal groove, which is narrowed or interrupted by the crosspiece in sections in the longitudinal direction. The gap preferably extends to a groove ground of the longitudinal groove. In particular, a gap may be formed on each side of the slide in the width direction. The sliding shaft, in particular the slide, can be cleaned through the gap. The gap is preferably elongated, i.e. extends in the longitudinal direction of the shaft. In particular, the gap may be formed/milled as a milled recess. In this way, for example in contrast to bores, a flatter surface can be created and, for example, the formation of burrs can be reduced. According to a further development of the preferred embodiment, a cleaning gap may be formed on both sides of the slide in the width direction in order to further improve the cleaning of the slide.

According to a preferred embodiment, the cleaning recess and the longitudinal groove may be formed in such a way that they are fluidically connected to each other when the slide is arranged in the longitudinal groove, in particular in a region in the longitudinal direction in which the slide rests on the groove ground of the longitudinal groove. This means that the cleaning recess has, for example, a greater width extension (i.e. a greater extension in the width direction of the shaft) than the slide or, respectively, than the longitudinal groove in the region of the pair of crosspieces. In other words, the fluidic connection is made via the groove ground, i.e. the contact area of the slide. This allows flow even when the slide is mounted in the longitudinal groove, and in particular in the region of the crosspieces, so that the sliding shaft can be cleaned without having to be disassembled.

According to a preferred embodiment, a longitudinal extension (i.e., an extension in the longitudinal direction of the shaft) of the cleaning recess in the depth direction of the groove of the shaft may decrease from the outside to the inside. Preferably, the longitudinal extension may decrease along a concave area of the shaft. In this way, sufficient stability of the shaft can be ensured in an advantageous manner. According to a preferred embodiment, a longitudinal extension (i.e. an extension in the longitudinal direction of the shaft) of the cleaning recess in the width direction of the shaft may increase from the outside to the inside or may be substantially constant. Preferably, the longitudinal extension may increase along the concave area of the shaft. According to a preferred embodiment, a width extension (i.e. an extension in the width direction of the shaft) of the cleaning recess may be constant in the depth direction of the shaft. That is, the cleaning recess extends along a plane area that is perpendicular to the width direction. Such a configuration of the cleaning recess has proven to be particularly advantageous in terms of manufacturability, stability and cleanability of the shaft.

For example, the cleaning recess may have the shape of a circular segment or elliptical segment in the longitudinal section perpendicular to the width direction, as already indicated above. In particular, the cleaning recess may have a symmetry plane in common with the crosspiece, in particular perpendicular to the longitudinal direction. For example, the cleaning recess may have the shape of a circular layer or a rectangle in a longitudinal section perpendicular to the depth direction. In this way, the cleaning recess can be incorporated simply by plunging a milling cutter.

According to a preferred embodiment, a longitudinal extension of the crosspiece in the depth direction of the shaft may increase from the outside to the inside, in particular from a groove opening to a groove ground of the longitudinal groove. Preferably, the longitudinal extension may increase along a concave lateral surface of the crosspiece. According to a preferred embodiment, a longitudinal extension of the crosspiece in the width direction of the shaft may increase from the inside to the outside or may be substantially constant. Preferably, the longitudinal extension may increase along the concave lateral surface of the crosspiece. Thus, the geometry of the crosspiece can be easily generated by milling.

According to a preferred embodiment, the through hole formed by the cleaning recess may have a greater width extension than the slide and/or the longitudinal groove in the region of the crosspiece. This allows the cleaning fluid to flow through.

According to a preferred embodiment, the through hole formed by the cleaning recess may have a greater longitudinal extension than the crosspiece in its shortest region, in particular at the groove opening, and/or a smaller longitudinal extension than the crosspiece in its longest region, in particular at the groove ground. Such a configuration has proven to be suitable in terms of only slightly reduced stability and sufficient flow rate.

According to a preferred embodiment, the sliding-shaft instrument may comprise a described sliding shaft and an instrument handle connected thereto for actuating the relative displacement of the slide and an effector/tool head/tool portion operable by the relative displacement of the sliding shaft. The instrument handle is attached to a proximal end of the sliding shaft. The instrument handle allows a relative displacement of the slide to be operable, in particular manually. The tool head is attached to a distal end of the sliding shaft. The relative displacement of the slide allows actuation of the tool head, in particular opening and closing of the tool head, to be operable.

In summary, the present disclosure relates to a surgical sliding-shaft instrument having a sliding shaft. The sliding shaft has a sliding guide and a sliding plate guided therein. Due to the tight guidance of the sliding plate, reproducible reprocessing of a reusable instrument is virtually impossible. With the aid of milled cutouts, free spaces can be created in the sliding guide in order to enable the instrument to be cleaned. Previous solutions, in which continuous holes are provided along the entire length of the sliding plate in the sliding guide, have the disadvantage that the sliding shaft has reduced stability, the effectiveness has not yet been proven, and the burrs of the holes are inconvenient and difficult to remove. Other solutions, in which recesses are provided on the upper side of the sliding shaft, enable improved cleaning behavior of the sliding plate, since a brush can be used to clean down to the depth. According to the present disclosure, a combination of milled cutouts from above with milled cutouts from below is provided in order to improve effectiveness. The milled cutouts on the sliding shaft from above and from below, and the remaining crosspieces ensure the function of the instrument, avoid kinking of the sliding plate (for example adjustable by the number of crosspieces), while the lower milled cutouts allow a flow between above and below.

DETAILED DESCRIPTION

Figure 1:
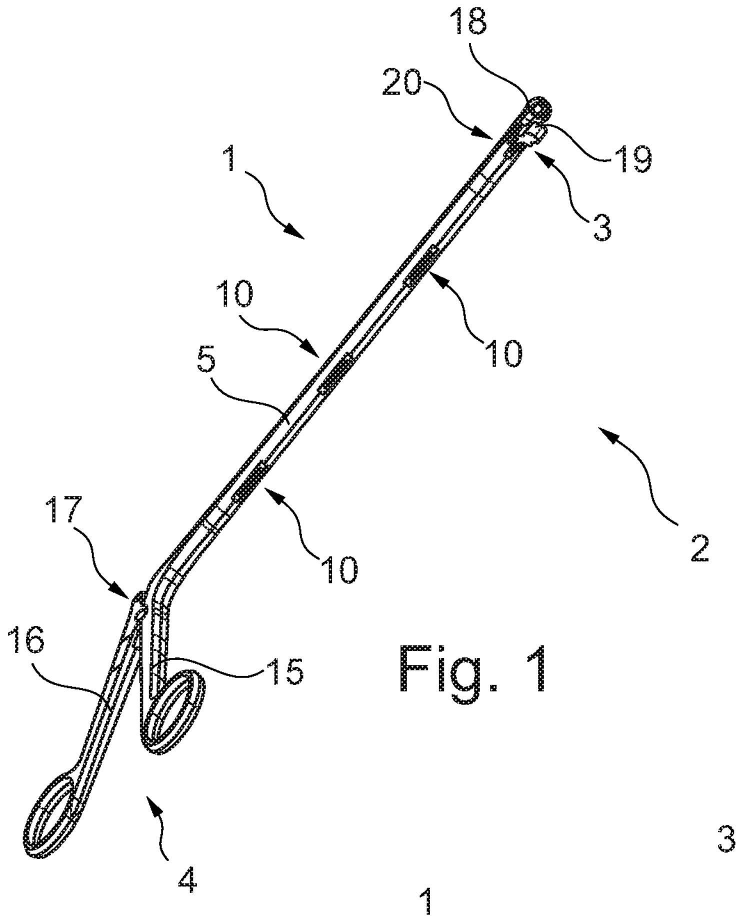
FIGS. 1 and 2 are perspective views of a sliding-shaft instrument with a sliding shaft.
Figure 2:
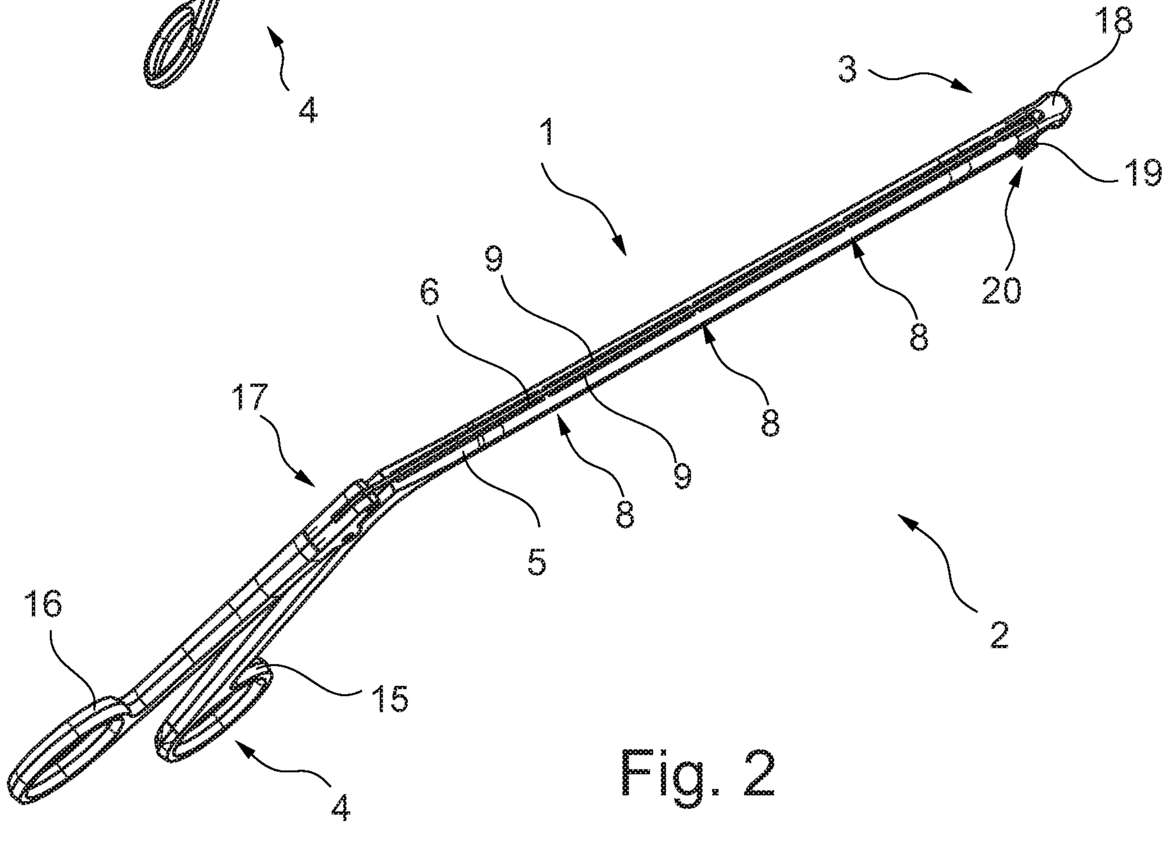

A preferred configuration example of the present disclosure is described below based on the accompanying figures.

FIGS. 1 to 6 show a preferred embodiment of a sliding shaft 1 or of a surgical sliding-shaft instrument 2, respectively. The sliding shaft 1 serves to couple an actuation of a tool head/tool portion 3 of the sliding-shaft instrument 2 arranged at a distal end of the sliding shaft 1 with an actuation of an instrument handle 4 of the sliding-shaft instrument 2 arranged at a proximal end of the sliding shaft 1.

The sliding shaft 1 has an elongated shaft 5 and a slide (/sliding plate) 6 displaceably arranged thereon. The actuation of the instrument handle 4, in particular a pivoting movement of the instrument handle 4, is coupled or couplable with a relative displacement of the slide 6 relative to the shaft 5. The relative displacement of the slide 6 in the longitudinal direction relative to the shaft is coupled or couplable with the actuation of the tool head 3, in particular a closing or opening movement of the tool head 3. In this way, the opening or respectively closing of the tool head 3 is achieved by the longitudinal movement of the slide 6 along the shaft 5.

The slide 6 is arranged in a longitudinal groove 7 of the shaft 5. The longitudinal groove 7 is open towards an upper side of the shaft 5. The slide 6 preferably extends in the form of a plate. The slide 6 extends in the longitudinal direction of the shaft 5 and in the depth direction of the shaft 5. I.e. a thickness of the slide 6 extends in the width direction of the shaft 5. The slide 6 extends over substantially the entire longitudinal extension of the longitudinal groove 7 of the shaft 5.

The slide 6 is arranged so as to be longitudinally displaceable in the longitudinal groove 7. The longitudinal groove 7 is preferably arranged centrally in the shaft 5 in the width direction. The slide 6 is preferably arranged centrally in the longitudinal groove 7 in the width direction. The relative displacement of the slide 6 is guided in sections by at least one crosspiece 8 of the shaft 5, which narrows the longitudinal groove 7 in the width direction. The crosspiece 8 thus forms a guiding surface for the slide 6. In particular, the slide 6 rests against the guiding surface of the crosspiece 8. In particular, the relative displacement of the slide 6 is guided by at least one pair of crosspieces 8 arranged opposite in the width direction. The pair of crosspieces 8 arranged opposite each other in the width direction (hereinafter also referred to as pair of crosspieces) may preferably be arranged spaced apart from each other by the thickness of the slide 6, i.e. its extension in the width direction of the shaft 5. Thus, the slide 6 may rest on both its sides against one respective crosspiece 8 of a pair of crosspieces.

In other words, the longitudinal groove 7 has a basic width corresponding to a distance between two crosspieces 8 of a pair of crosspieces or a thickness of the slide 6, respectively. In addition, the longitudinal groove 7 has a greater width than the basic width in sections along the longitudinal direction, i.e. the longitudinal groove 7 widens in sections. In the widened sections of the longitudinal groove 7, the slide 6 is not guided by the shaft 5. Thus, a gap 9 is formed in the widened sections between the slide 6 and the shaft 5. The gap 9 can be regarded as a part of the longitudinal groove 7. The gap 9 preferably extends to a groove ground of the longitudinal groove 7. In particular, a gap 9 may be formed on both sides of the slide 6 in the width direction. The sliding shaft 1, in particular the slide 6, can be cleaned through the gap 9. The gap 9 is preferably elongated, i.e. extends in the longitudinal direction of the shaft 5. In particular, the gap 9 may be formed/milled as a milled cutout. In this way, for example in contrast to bores, a flatter surface can be created and, for example, the occurrence of burrs can be reduced.

This means that the longitudinal groove 7 widens along the longitudinal direction in sections in the width direction (by the gap 9) or narrows/becomes smaller in sections in the width direction (by the crosspiece 8). The gap 9 is thus narrowed or interrupted in sections in the longitudinal direction by the crosspiece 8.

Depending on the length of the sliding shaft 1 (and/or the thickness of the slide 6), the shaft 5 has multiple crosspieces 8 (or pairs of crosspieces) spaced apart in the longitudinal direction along the longitudinal groove 7. Preferably, the multiple crosspieces 8 (or pair of crosspieces) are spaced at equal intervals in the longitudinal direction. This prevents the slide 6 from kinking.

According to the present disclosure, the shaft 6 has a cleaning recess 10 which forms a through hole opening into the longitudinal groove 7. The cleaning recess 10 is arranged in the longitudinal direction in the region of the crosspiece 8. The cleaning recess 10 is open towards a lower side of the shaft 5. By forming a passage between the cleaning recess 10 and the longitudinal groove 7, a flow of cleaning fluid, for example from top to bottom or from bottom to top, through the shaft 5 and around the slide 6 is made possible. Due to the arrangement of the cleaning recess 10 in the region of the crosspiece 8, the stability of the shaft 5 is only insignificantly reduced. Preferably, the shaft 5 has several cleaning recesses 10, in particular one cleaning recess 10 per crosspiece 8 (or pair of crosspieces).

The cleaning recess 10 is preferably elongated, i.e. extends in the longitudinal direction of the shaft 5. In this way, as little material as possible is removed from the shaft 5 in its more unstable width direction for the cleaning recess 10. Preferably, the cleaning recess 10 may be formed/milled as a milled cutout. In this way, for example in contrast to bores, a more planar surface can be produced and, for example, the occurrence of burrs can be reduced. The cleaning recess 10 is preferably arranged centrally in the shaft 5 in the width direction.

The cleaning recess 10 and the longitudinal groove 7 may in particular be formed in such a way that they are fluidically connected to each other when the slide 6 is arranged in the longitudinal groove 7. This means, for example, that the cleaning recess 10 has a greater width extension (i.e. a greater extension in the width direction of the shaft 5) than the slide 6 or respectively than the longitudinal groove 7 in the region of the pair of crosspieces 8. This allows flow even when the slide 6 is mounted in the longitudinal groove 7.

Figure 3:
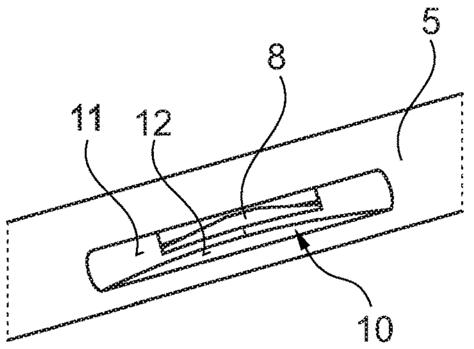
FIGS. 3 and 4 are perspective views of a detail of a shaft of the sliding shaft.

A preferred shape of the cleaning recess 10 is shown enlarged in FIG. 3. A longitudinal extension (i.e. an extension in the longitudinal direction of the shaft 5) of the cleaning recess 10 may decrease from the outside to the inside in the depth direction of the shaft 5. In particular, the cleaning recess 10 may have the shape of a circular segment or elliptical segment in a longitudinal section (perpendicular to the width direction of the shaft 5). For example, the longitudinal extension of the cleaning recess 10 can thus decrease along a concave area 11 of the shaft 5 from the outside (here below) to the inside (here above). The longitudinal extension (i.e. an extension in the longitudinal direction of the shaft 5) of the cleaning recess 10 may increase in the width direction of the shaft 5 from the outside to the inside. For example, the longitudinal extension of the cleaning recess 10 may increase along the concave area 11 of the shaft 5 in the width direction from the outside to the inside. In particular, the cleaning recess 10 may have the shape of a circular layer or an elliptical layer in the longitudinal section (perpendicular to the depth direction of the shaft 5). A width extension (i.e. an extension in the width direction of the shaft 5) of the cleaning recess 10 may preferably be constant in the depth direction of the shaft 5. That is, the cleaning recess 10 extends along a plane area 12 that is perpendicular to the width direction. Preferably, the cleaning recess 10 and the crosspiece 8 (or the pair of crosspieces) are substantially symmetrical to a common plane of symmetry perpendicular to the longitudinal direction and/or to a common plane of symmetry perpendicular to the width direction.

Figure 4:
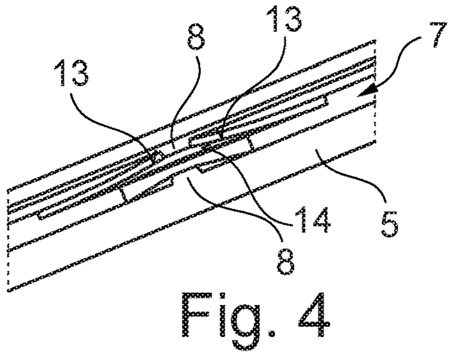

A preferred shape of the crosspiece 8 is shown enlarged in FIG. 4. A longitudinal extension (i.e. an extension in longitudinal direction of the shaft 5) of the crosspiece 8 may increase in the depth direction of the shaft from the outside to the inside. That is, the longitudinal extension of the crosspiece 8 may in particular increase from a groove opening to the groove ground of the longitudinal groove. In particular, the crosspiece 8 may have the shape of a circular segment or elliptical segment in a longitudinal section (perpendicular to the width direction of the shaft 5). For example, the longitudinal extension of the crosspiece 8 may thus increase along a concave lateral surface 13 of the crosspiece 8 from the outside (here above) to the bottom (here below). The longitudinal extension (i.e., an extension in the longitudinal direction of the shaft 5) of the crosspiece 8 may increase in the width direction of the shaft 5 from the inside to the outside. For example, the longitudinal extension of the crosspiece 8 may thus increase along the concave lateral surface 13 of the crosspiece 8 in the width direction from the inside to the outside. A width extension (i.e., an extension in the width direction of the shaft 5) of the crosspiece 8 may preferably be constant in the depth direction of the shaft 5. That is, the crosspiece 8 extends along a plane area 14 that is perpendicular to the width direction. The plane area 14 of the crosspiece 8 serves as a guiding surface for the slide 6.

Figure 5:
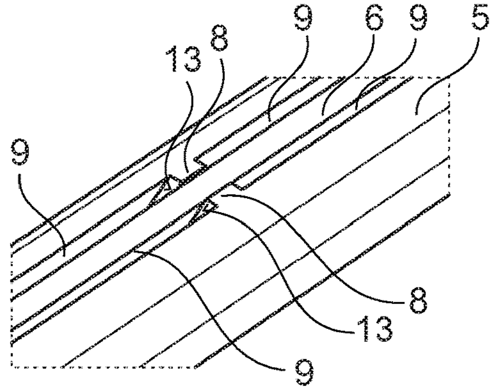
FIG. 5 is a perspective view of the detail of FIG. 4 with a slide housed in the shaft.

FIG. 5 shows the section of FIG. 4, wherein the slide 6 is arranged in the longitudinal groove 7 of the shaft 5. It can be seen that the gap 9 is formed on both sides of the slide 6 in the width direction. The gap 9 has essentially the same width extension as the crosspiece 8. The slide 6 is in contact with the shaft 5 only in the area of the crosspiece 8.

Figure 6:
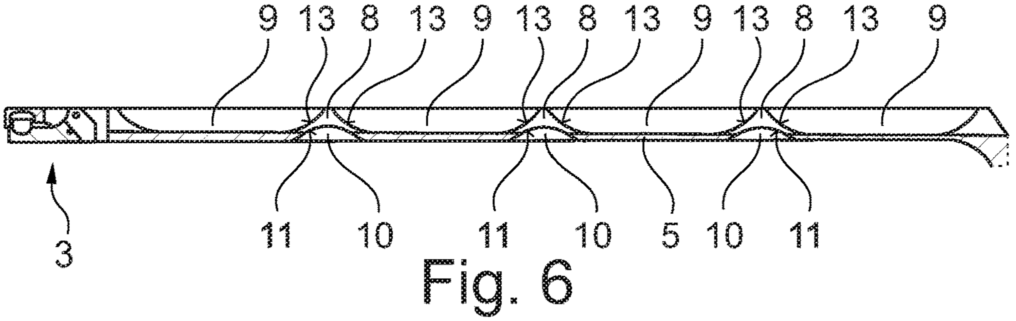
FIG. 6 is a sectional view of the sliding-shaft instrument.

FIG. 6 shows a longitudinal section of the sliding shaft 1, perpendicular to a width direction of the shaft 5. It can be seen that the cleaning recesses 10 on the lower side of the shaft 5 extend into the shaft 5 in the depth direction so far that they open into the longitudinal groove 7. This forms the through hole in the region of the crosspieces 8. The gap 9 is interrupted by the crosspiece 8 so that the gap extends over the concave lateral surfaces 13 to the groove ground of the longitudinal groove 7. That is, an outlet of the gap 9 is circular arc-shaped in a longitudinal section. This results in a bridge-like shape of the crosspiece 8 in a longitudinal section, which is bounded by the two concave lateral surfaces 13 and the concave area 11. The concave area 11 has essentially the same curvature as the concave lateral surfaces 13.

For actuating the surgical sliding-shaft instrument 2, the instrument handle 4 is formed by two hand grips 15, 16 which are pivotable relative to each other. A first hand grip 15 may be firmly connected to the shaft 5. A second hand grip 16 may be operatively connected to the slide 6, for example via a hinge 17, in such a way that it displaces the slide 6 relative to the shaft 5 in the longitudinal direction when the second hand grip 16 is pivoted relative to the first hand grip 15. The tool head 3 is formed by two tool parts 18, 19 that are pivotable relative to each other. A first tool part 18 may be firmly connected to the shaft 5. A second tool part 19 may be operatively connected to the slide 6, for example via a hinge 20, in such a way that a relative displacement of the slide 6 relative to the shaft 5 pivots the second tool part 19 relative to the first tool part 18, in particular opening or closing the tool head 3.

The invention claimed is:

1. A hand-held surgical instrument comprising:

an elongated shaft having a longitudinal groove extending along the elongated shaft along a length direction, a width direction transverse to the length direction, and a depth direction transverse to the length direction and the width direction, wherein the longitudinal groove extends in the depth direction from a first side of the elongated shaft to a groove ground located between the first side of the elongated shaft and a second side of the elongated shaft, the second side being opposite the first side; and a slide, which is mounted displaceably in the longitudinal groove, displacement of the slide in the longitudinal groove along the length direction being guided in sections by at least one crosspiece of the elongated shaft that narrows the longitudinal groove in the width direction, the elongated shaft comprising, in a region of the at least one crosspiece, a cleaning recess comprising a radial through hole that extends in the depth direction to form an open passage from the groove ground to the second side of the elongated shaft wherein a longitudinal dimension of the at least one crosspiece along the length direction increases in the depth direction from the first side of the elongated shaft to the groove ground, and wherein the at least one crosspiece extends in the depth direction from the first side of the elongated shaft to the groove ground.

2. The hand-held surgical instrument according to claim 1, further comprising a gap for cleaning formed in the width direction between the slide and the elongated shaft.

3. The hand-held surgical instrument according to claim 2, wherein the gap is formed on both sides of the slide in the width direction.

4. The hand-held surgical instrument according to claim 1, wherein the cleaning recess and the longitudinal groove are fluidically connected to each other when the slide is arranged in the longitudinal groove, in a region along the length direction in which the slide rests on the groove ground of the longitudinal groove.

5. The hand-held surgical instrument according to claim 1, wherein a longitudinal dimension of the cleaning recess along the length direction decreases from the second side of the elongated shaft towards the groove ground.

6. The hand-held surgical instrument according to claim 5, wherein the cleaning recess comprises a circular segment or elliptical segment extending in the length direction as viewed perpendicular to the length direction and perpendicular to the depth direction.

7. The hand-held surgical instrument according to claim 1, wherein a longitudinal dimension of the at least one crosspiece along the length direction increases in the width direction away from a centerline of the longitudinal groove along the length direction.

8. The hand-held surgical instrument according to claim 1, wherein the radial through hole has a respective width dimension along the width direction, the slide has a respective width dimension along the width direction, and the longitudinal groove has a respective width dimension along the width direction, and the respective width dimension of the radial through hole is greater, in the region of the at least one crosspiece, than the respective width dimension of the slide and/or the respective width dimension of the longitudinal groove.

9. The hand-held surgical instrument according to claim 1, further comprising an instrument handle attached to a proximal end of the elongated shaft, the instrument handle allowing a relative displacement of the slide to be operable, and an effector attached to a distal end of the elongated shaft and being operable by the relative displacement of the slide.

10. The hand-held surgical instrument according to claim 5, wherein the cleaning recess is defined in a concave area of the elongated shaft.

11. The hand-held surgical instrument according to claim 1, wherein the at least one crosspiece has a concave lateral surface, and the longitudinal dimension of the at least one crosspiece along the length direction increases in the depth direction from the first side of the elongated shaft to the groove ground along the concave lateral surface of the at least one crosspiece.

12. The hand-held surgical instrument according to claim 7, wherein the at least one crosspiece has a concave lateral surface, and the longitudinal dimension of the at least one crosspiece along the length direction increases in the width direction away from the centerline of the longitudinal groove along the length direction along the concave lateral surface of the at least one crosspiece.

13. The hand-held surgical instrument according to claim 1, wherein a longitudinal dimension of the cleaning recess along the length direction increases in the width direction from the second side of the elongated shaft towards the groove ground.

14. The hand-held surgical instrument according to claim 1, wherein a longitudinal dimension of the cleaning recess along the length direction remains constant in the width direction from the second side of the elongated shaft towards the groove ground.

* * * * *